United States Patent [19]

Grundei et al.

[11] Patent Number: 5,005,564
[45] Date of Patent: Apr. 9, 1991

[54] CERVICAL SUPPORT

[75] Inventors: Jaana Grundei, Lübeck; Andreas Timmermann, Ekelsdorf, both of Fed. Rep. of Germany

[73] Assignee: ADEV Gesellschaft fur Entwicklung und Vertrieb von medizintechnishen Artikein mbH, Lubeck, Fed. Rep. of Germany

[21] Appl. No.: 479,090

[22] Filed: Feb. 12, 1990

[30] Foreign Application Priority Data

Feb. 28, 1989 [DE] Fed. Rep. of Germany ....... 3906232

[51] Int. Cl.5 .......................... A61H 1/02; A61F 5/04
[52] U.S. Cl. ..................................... 128/75; 128/87 B; 128/DIG. 23; 128/DIG. 15
[58] Field of Search ................. 128/87 A, 87 B, 87 C, 128/76 R, 78, 75, DIG. 23, 87 R, 77, DIG. 15; D24/64

[56] References Cited

U.S. PATENT DOCUMENTS

| | | | |
|---|---|---|---|
| 2,818,063 | 12/1957 | Smith | 128/82 B |
| 3,050,052 | 8/1962 | Grassl | 128/75 |
| 3,530,853 | 9/1970 | Bond | 128/87 B |
| 3,916,885 | 11/1975 | Gaylord, Jr. | 128/75 |
| 4,099,523 | 7/1978 | Lowrey | 128/75 |
| 4,232,663 | 11/1980 | Newton | 128/75 |
| 4,520,801 | 6/1985 | Lerman | 128/87 B |
| 4,582,051 | 4/1986 | Greene | 128/87 B |
| 4,677,969 | 7/1987 | Calabrese | 128/87 B |
| 4,708,129 | 11/1987 | Pujals | 128/87 B |
| 4,712,540 | 12/1987 | Tucker | 128/75 |
| 4,854,306 | 8/1989 | Pujals | 128/87 B |
| 4,886,052 | 12/1989 | Calabrese | 128/75 |

Primary Examiner—Robert A. Hafer
Assistant Examiner—Michael Brown
Attorney, Agent, or Firm—Dvorak and Traub

[57] ABSTRACT

A cervical support has a substantially inherently stable support member of resilient foam material, constructed to encircle the neck of a patient who is to wear the cervical support. The support member has overlapping free end parts which are releasably connectable to each other. Support elements are insertable into through radial openings of the support member, each support element having a shank having a mushroom-shaped head at one end and a large area head at its other end. The former head can be pressed into a disc or band partially embracing the outer surface of the support member. The support elements can be selectively removed from, or inserted into, the openings to provide local stiffening of the support member as required by the patient's condition.

6 Claims, 4 Drawing Sheets

CERVICAL SUPPORT

FIELD OF THE INVENTION

This invention relates to a cervical support comprising a substantially inherently stable support member of a resilient foam material and which may be provided with a covering of textile material. The support member is constructed to encircle the neck of a patient who is to wear the cervical support and has free end parts which overlap each other in a nape support region thereof and are releasably connectable to each other. Two jaw support regions of the support member have upper and lower edges contoured to fit the patient's chin or the region of the patient's body proximate to the neck. The shape of the support member is partially stabilisable by means of support elements which are releasably connectable thereto.

BACKGROUND OF THE INVENTION

Such a cervical support is disclosed in DE-B-24 04 683. Although this cervical support has proved to be successful in practice the partially stabilising means lack adaptability to the requirements of the patient's condition.

The problem of such lack of adaptability is not solved in the case of a cervical support which is disclosed in DE-U-70 46 248. This cervical support, which is adapted to the neck and shoulder parts is divided by a vertically disposed, releasable fastener. Since the cervical support is made of leather or of a textile material built in and/or removable stiffening elements are provided to compensate for the lack of rigidity of the material of the cervical support.

SUMMARY OF THE INVENTION

It is an object of the invention to provide a cervical support which is adjustable in accordance with the patient's condition and which is readily adaptable to changing requirements during the course of therapy.

To this end the support member is formed with at least one radial opening for receiving a support element having a shank which is insertable into the opening and thereby passes through the support member, and a large area head which comes into abutment with the inner circumferential surface of the support member and stiffens it at that location.

The patient's different symptoms can accordingly be taken into account. Thus, for example, to provide an easy resting position and relatively slight support by the cervical support, near to the end of the patient's treatment, no support element is assembled to the support member which then has primarily a heating function. Under other circumstances, however, support elements may be assembled to the support member, for example to provide a resting position with a strong support function or a strong resting position with the cervical support greatly stiffened.

The support elements for locally stiffening the support member are preferably releasably secured thereto. To this end, when a support element is in its assembled state, the shank of each support element may have an end which projects outwardly from the support member beyond the outer circumference thereof and which can be releasably anchored in a flexible band which abuts, and partially embraces, the outer surface of the support member. For this purpose, an end of the shank may be formed with a mushroom-shaped enlarged head and may extend through a respective opening in the band, which opening is dimensioned to correspond to the cross-sectional area of the shank so that the mushroom-shaped head can be snapped into the opening.

DETAILED DESCRIPTION OF THE INVENTION

Figure 1:
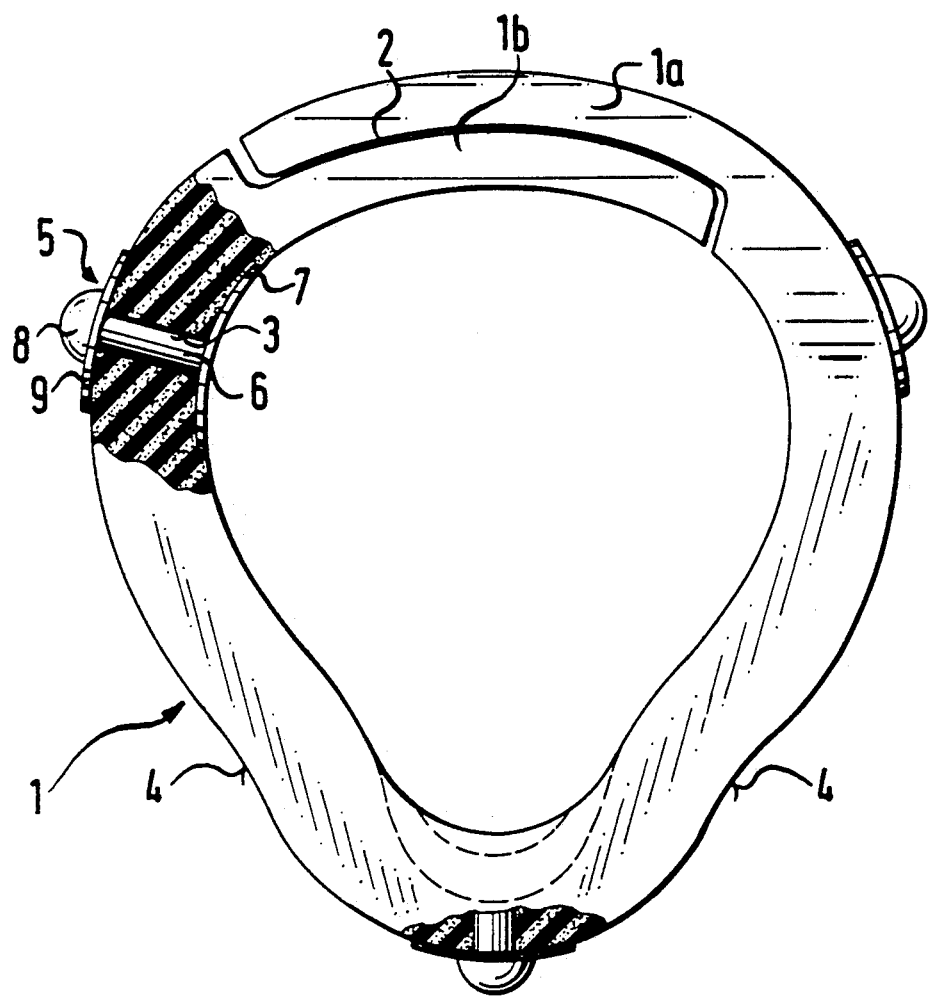
FIG. 1 is a plan view, shown partly in section of a cervical support provided with three support elements.

A cervical support comprises a flexible and substantially inherently stable support member 1 made of a resilient foam material and which is constructed to be placed about the neck of a patient who is to wear it and to adapt itself to the anatomy of the patient. The support member 1 has end parts 1a and 1b (FIGS. 1 and 2) which overlap about the patient's neck and are held in overlapping relationship by fastener means, preferably by means of hook-and-loop fastener means 2. Even when the cervical support is not in use, the inherent stability of the support member 1 is such that it is circumferentially stable, the flexibility of the support member 1 being such that it can be spread apart in its nape of the neck region for the purpose of applying the cervical support to the patient's neck and removing it therefrom. The resilience of the support member 1 is such that the cervical support is self-closing after being spread apart as aforesaid.

Figure 3:
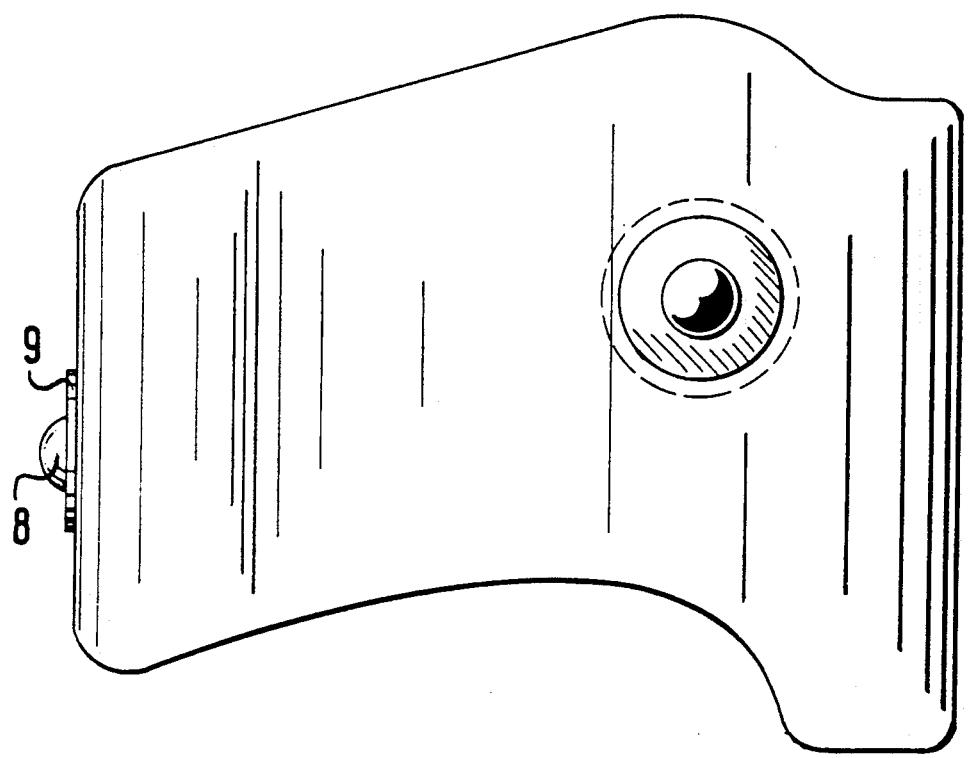
FIG. 3 is a side view of the cervical support of FIG. 1.
Figure 4:
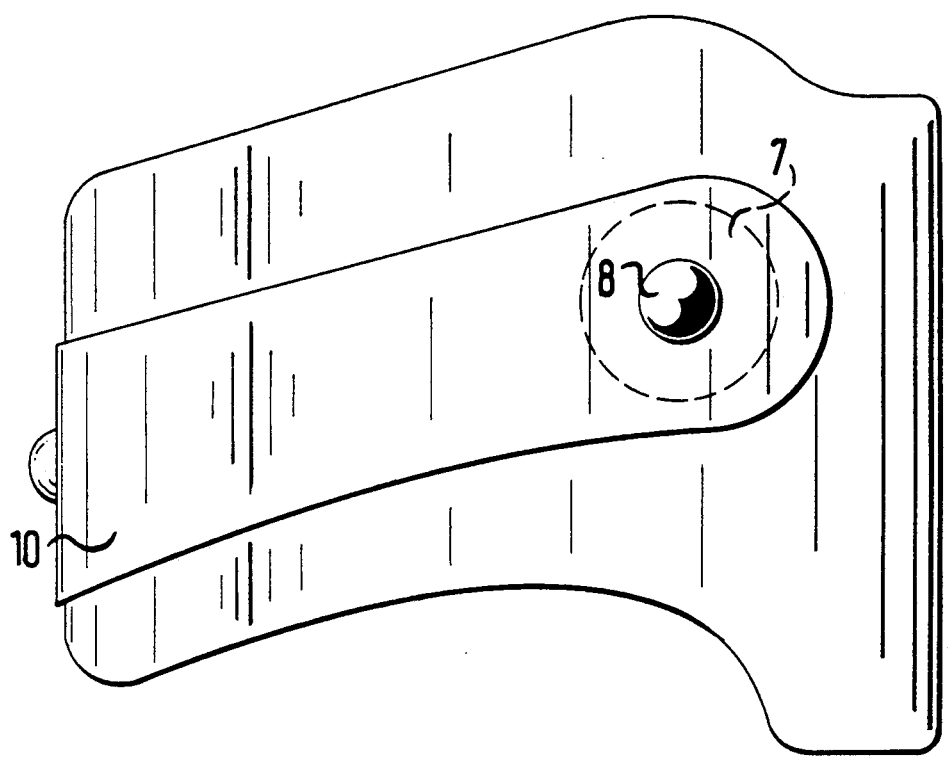
FIG. 4 is a side view of the cervical support of FIG. 2.

As best seen in FIGS. 3 and 4, the upper and lower circumferential edges of the cervical support are substantially adapted to the shape of the patient's head, and shoulder regions adjacent to the neck. In the present embodiment, the support member 1 is formed with three radial, through openings 3, although further such openings may also be provided, for example in the region of concave indentations 4 in the outer circumferential surface of the support member 1.

Figure 2:
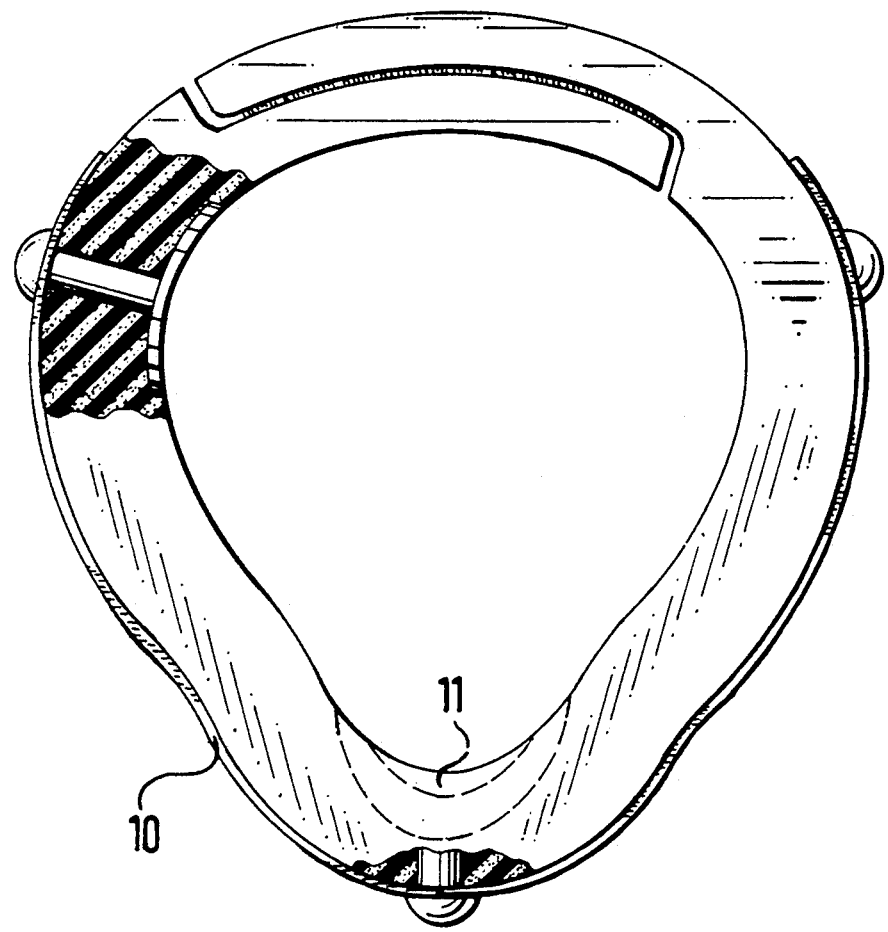
FIG. 2 is a similar view to that of FIG. 1, but also showing a stiffening band extending about the outer circumference of the cervical support and having a support element anchored therein.

Each opening 3 receives a support element 5 having a shank 6 one end of which is provided with a disc-shaped, large area head 7 and the other end of which is formed with an enlarged head 8 shaped as a mushroom head. Each element 5 is preferably made from a flexible but semi-stiff, plastics material. The head 8 of each element 5 is selectively pressable into a central bore of a disc 9 which may be made of a similar material to that of the element 5. There may be substituted for the discs 9, a flexible band 10 which, as shown in FIGS. 2 and 4, abuts against, and embraces, partially, the outer circumferential surface of the support member 1. The band 10 is recessed so as to be set back from the end parts 1a and 1b, and is formed with bores each aligned with a respective opening 3, which bores receive the heads 8 of the elements 5.

The shank 6 of each element 5 is of such length that the head 7 thereof lies flush with the internal surface of the support member 1 after fixing it in position by pressing the head 8 of the element 5 into the disc 9 or the band 10 as the case may be. The internal surface of the support member 1 is formed with a depression 11, FIGS. 1 and 2, in that part of the member 1 which is proximate to the patient's larynx when the cervical support is in use, so that the head 7 of the element 5 at that location is countersunk thereby leaving clearance for the larynx.

Elements 5 are provided, as needed in the openings 3 for locally stiffening the support member 1 where this is thought to be therapeutically helpful at the time, in accordance with the diagnosis of the patient's symptoms. When the cervical support has been so adjusted, it is lined with a skin compatible textile covering which may be provided with the fastener means 2 in the region of the end parts 1a and 1b.

During therapy, the said local stiffening may be reduced as the patient's condition improves, by removing individual support elements 5 or replacing the band 10 when such is in use, by discs 9.

What is claimed is:

1. A cervical support comprising:
   a substantially inherently stable support member of resilient foam material for encircling the neck of a patient and having a nape support rear region, two lateral jaw support regions extending from a larynx region, said jaw support regions terminating in free end parts which overlap each other in said nape support region; and jaw support regions having upper and lower edge contours adapted to the anatomical shape of the parts of the patient's body to which said contours are adjacent when the cervical support is in use;
   means for adjustably and releasably connecting said free end parts together in said nape support region; and locally stabilizing support means releasably connectable to the support member, said stabilizing support means comprising at least one support element having a shank which has one end insertable into a radial opening in said support member to extend therethrough, said shank having a large area head for abutment against the inner circumference of the support member to locally stiffen the support member, the other end of said shank adapted to abut the outer circumference of said support member.

2. A cervical support as claimed in claim 1, comprising means for releasably securing said at least one support element in said support member.

3. A cervical support as claimed in claim 1, wherein said other end of said shank projects outwardly beyond the circumference of the support member when said support element is in use, a flexible band abutting the outer surface of the support member and partially embracing it, said other end being releasably attached to said flexible band.

4. A cervical support as claimed in claim 3, wherein said other end of the shank has a thickened mushroom-head configuration, the band having an opening through which said shank extends, said opening having a cross-section area slightly less than the cross-section area of said mushroom head.

5. A cervical support as claimed in claim 1, wherein said support member is provided with a covering of textile material.

6. A cervical support as claimed in claim 1, wherein the length of the shank is much shorter than the thickness of said foam material to draw said large area head into said foam material so that the head is flush with the surface of the foam material.

* * * * *